United States Patent
Baldwin (10) Patent No.: US 9,049,983 B1
(45) Date of Patent: Jun. 9, 2015

(54) EAR RECOGNITION AS DEVICE INPUT (75) Inventor: Leo B. Baldwin, Seattle, WA (US)

(73) Assignee: AMAZON TECHNOLOGIES, INC., Reno, NV (US)

(*) Notice: Subject to any disclaimer, the term of this patent is extended or adjusted under 35 U.S.C. 154(b) by 789 days.

(21) Appl. No.: 13/083,330

(22) Filed: Apr. 8, 2011

(51) Int. Cl.
H04N 7/18 (2006.01)
A61B 1/00 (2006.01)

(52) U.S. Cl.
CPC .................. A61B 1/00039 (2013.01)

(58) Field of Classification Search
None
See application file for complete search history.

(56) References Cited

U.S. PATENT DOCUMENTS

2007/0036398 A1* 2/2007 Chen .............................. 382/118
2008/0285813 A1* 11/2008 Holm ............................ 382/115
2008/0307463 A1* 12/2008 Beetcher et al. ................ 725/53
2009/0061819 A1* 3/2009 Coughlan et al. ............. 455/410
2009/0167678 A1* 7/2009 Orr et al. ....................... 345/156
2010/0167795 A1* 7/2010 Huang .......................... 455/567
2010/0171846 A1* 7/2010 Wood et al. ............... 348/231.99
2010/0333128 A1* 12/2010 Smith et al. ..................... 725/25
2011/0029579 A1* 2/2011 Lions ........................... 707/809

* cited by examiner

Primary Examiner — Sath V Perungavoor
Assistant Examiner — Kate Luo
(74) Attorney, Agent, or Firm — Novak Druce Connolly Bove + Quigg LLP (57) ABSTRACT An electronic device can attempt to capture at least one image including at least a portion of a user's ear when the user utilizes the electronic device for certain purposes, such as to receive a call or listen to an audio file. In some embodiments, the device analyzes the captured information to determine whether the user is holding the device near the user's right ear or left ear, and adjusts functionality of the device based at least in part upon how the user is likely holding the phone. In other embodiments, the device attempts to recognize the user based on ear shape or other parameters, and can provide customized functionality of the device based at least upon that determination.

24 Claims, 5 Drawing Sheets

EAR RECOGNITION AS DEVICE INPUT

BACKGROUND

As technology advances, people are increasingly expecting electronic devices to offer capabilities that are able to be personalized or at least offer flexibility in the types of available functionality. While various software applications offer differing levels of personalization, many electronic devices such as cellular phones and tablet computers still have fixed inputs for various buttons or other input elements of the device. Even where some level of personalization is enabled, such as at various levels of a user interface, the user typically must login or enter other identifying information for the device, which can be frustrating if the user needs to repeatedly enter the information. Some interfaces enable a user to stay logged in, but such an approach prevents different users from easily accessing personalized functionality.

BRIEF DESCRIPTION OF THE DRAWINGS

Various embodiments in accordance with the present disclosure will be described with reference to the drawings, in which.

DETAILED DESCRIPTION

Systems and methods in accordance with various embodiments of the present disclosure may overcome one or more of the aforementioned and other deficiencies experienced in conventional approaches to enabling an electronic device to quickly recognize at least some aspect of a user. Various embodiments also enable the electronic device to adjust various functionality based at least in part upon the recognized aspect.

In at least some embodiments, an electronic device such as a cellular phone or smart device is able to capture one or more images of a portion of a user. The images can be captured using any appropriate image capture element, such as a still camera, video camera, heat signature detector, or other such device. The images can be analyzed to attempt to locate at least one feature of a user, such as one of the user's ears.

In certain embodiments, the device can attempt to determine whether the device is being brought into proximity with the right ear or left ear of a user. In at least some embodiments, the device can change at least some of the functionality of the device based at least in part upon which of the ears the device is near. For example, a user holding the device near a right ear likely is using the user's right hand, such that the user's thumb is likely in a particular area on the device, and the user is more apt to want to provide input using a certain button on the device. Accordingly, the device might assign certain inputs to certain buttons on the device that are more convenient for a user holding the device in a right hand. Similarly, a user holding the device near a left ear is likely holding in a left hand, which can cause the device to switch some of the functionality to buttons or inputs on the other side of the device. Various other changes can be made as well.

In certain embodiments, an electronic device can attempt to identify a user of the device. The shape of a person's ear can be relatively unique, similar to a fingerprint, and thus can be used to identify or authenticate a user of the device. In some embodiments, a user must be identified as an authorized user before being set and/or granted access to certain functionality or data. In other embodiments, various settings of the device might be altered based upon the identity of the user. For example, the functionality of various buttons or ring tones of the device might depend upon the identity of the user.

In some embodiments, the device can utilize the ear information to attempt to determine a relative distance between the device and the user. If, for example, the device is to be kept at a target distance (or range of distances) from the user, the device can use the captured ear information to attempt to determine a relative distance between the device and the user. In some embodiments, the device can adjust a speaker volume or other such aspect in order to attempt to cause the user to adjust the relative distance.

Various other applications, processes and uses are presented below with respect to the various embodiments.

Figure 1:
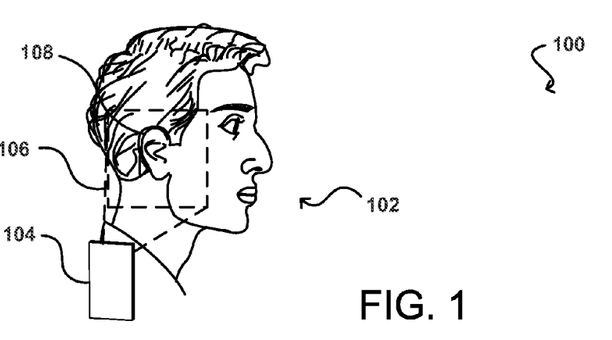
FIG. 1 illustrates an environment in which a user is able to interact with an electronic device in accordance with various embodiments.

FIG. 1 illustrates an example situation 100 wherein a user 102 of an electronic device 104 is moving and/or holding the device near the user's ear 108. In one example, the device 104 could be a smart phone that the user is moving towards the user's ear in order to have a conversation with another person via the phone. The device 104 can have at least one imaging element at least partially facing the user during operation, such that while the user is bringing the device near the user's ear, the imaging element is able to capture an image of a viewing area 106 including at least a portion of the user. During at least some types or modes of operation or movement, the viewing area will contain the user's ear, or another such feature. It should be understood that other use cases might provide such views as well, such as where the user 102 positions an electronic device near the user's ear to listen to audio produced by the device.

Figure 2A:
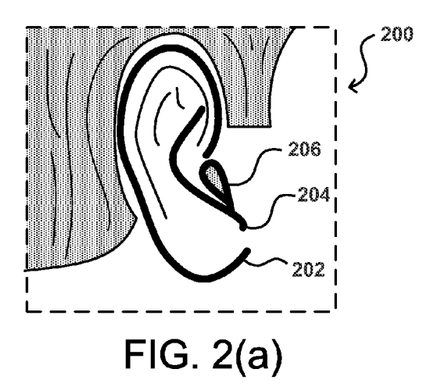
FIGS. 2(a)-2(d) illustrate example approaches for matching captured ear information to stored ear-related information that can be used in accordance with various embodiments.

FIG. 2(a) illustrates an example of such an image 200 including at least a portion of the user's ear. In at least some embodiments, the device will capture multiple images and/or video that can be analyzed to attempt to locate a user's ear in the captured image information. For example, the device might capture video when the device detects a certain type of movement, as may be determined using at least one orientation or position-determining element such as an accelerometer, electronic gyroscope, or inertial sensor. The device can utilize at least one image recognition or pattern recognition algorithm to attempt to locate at least part of an ear in at least one image frame. It should be understood, however, that in other embodiments the device could send the image information to a remote system or service to attempt to locate an ear or other aspects in the image information.

Figure 2B:
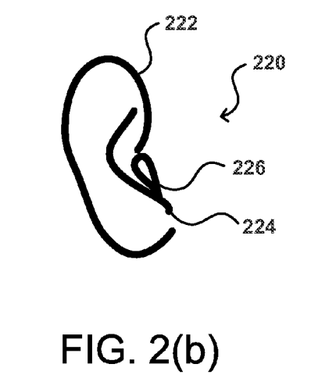

In one example, FIG. 2(b) illustrates a type of pattern 220 that the device might use to attempt to locate an ear in at least one image. In some embodiments, the pattern 220 might only include an outer portion 222 following the contour of the outer edge of a right ear. As should be understood, there can be a range or selection of ear shapes that can be used for matching. An algorithm can attempt to match the contour 222 with portions of one or more images. In at least one 200 of the captured images in this example, a match is found where the contour 202 matches the pattern contour 222 with at least an acceptable matching criterion or threshold to indicate that the image contains an ear. In this example, the matching indicates that the ear is a right ear, which can be used to set or adjust certain functionality or aspects as discussed subsequently.

As part of the same process or another process, the device in at least some embodiments can also attempt to recognize or identify the user based on information about the user's ear. For example, at least one pattern 220 stored can be specific to a user's ear, as may have been captured previously during a calibration or identification process. A person's ear is similar to a person's fingerprint in that it contains a relatively unique set of shapes, points, or features that can be used to identify a person with a relatively high degree of certainty. In this example, the pattern contains the shape of the user's outer ear contour 222, an inner ear contour 224, and the shape and relative position of the opening of the user's ear canal 226. By matching these contours to the respective contours (202, 204, 206) in the captured image 200, the device can further identify the user based on the captured image information. In at least some embodiments, the identification portion of the process is not started until at least one image is detected to likely have information corresponding to an ear, such that the amount of processing needed is reduced.

It should be understood that any appropriate feature, shape, or collection thereof can be used to match information with information for a user's ear. Further, the matching can be done using any appropriate matching algorithm or process used for locating pattern matches in image information. Further still, although contours are used in this example it should be understood that full images or other renderings of a user's ear can be used for matching purposes. Using contours provides the advantage that the uniqueness of a person's ear is still represented relatively accurately, while the amount of processing that has to be done for the matching can be significantly reduced with respect to full image matching. Further, image matching can be hampered by things like lighting conditions and partial obstructions or coverage, which can have less effect on contour matching under at least some conditions.

Figure 2C:
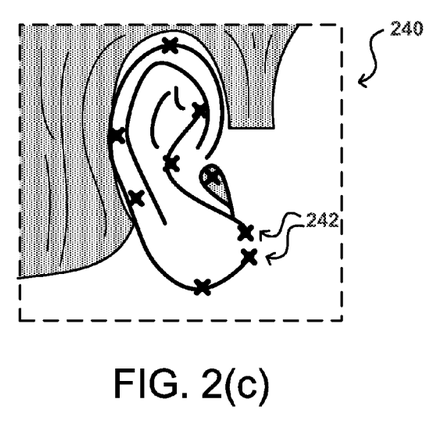
Figure 2D:
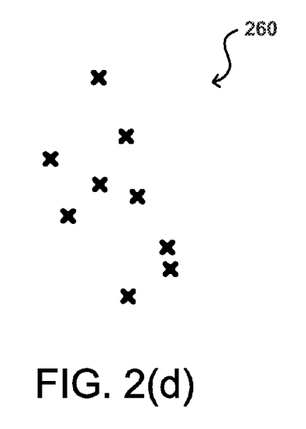

FIG. 2(c) illustrates another example matching approach that can be used in accordance with various embodiments. In this example, at least one captured image 240 is analyzed to attempt to determine the location of specific features of a user's ear. In this example, the locations are represented by markers 242 that each represent some aspect of the user's ear, such as the end of a contour or a point representing a change in curvature. Various other points, locations, or features can be determined as well using algorithms similar to those, for example, used to analyze unique features of fingerprints. Once a set of points 242 is determined for the captured image 240, those points can be used to attempt to find a match with ear pattern information for a user, such as the set of points 260 illustrated in FIG. 2(d). Such an approach can still provide a level of accuracy that is likely sufficient for distinguishing between a relatively small set of users, and can be much faster than other image or contour matching approaches discussed above. Feature-based matching does not require storing large data files, and can instead rely on the matching of points, distances, lines, relative arrangements, branching, looping, etc. It should be understood, however, that any of a number of other algorithms or approaches for identifying a user's ear can be used as well within the scope of the various embodiments.

As mentioned above, a user will often hold a phone or other device near a user's ear for certain uses, but will not often hold that device in a position to get a complete frontal view of the user's face for purposes of image matching. Matching based on a user's ear avoids the need for such capture, and can be much faster and less resource intensive than attempting to match a user's face, which further can be obstructed by glasses, facial hair, etc. The ability to recognize a person based on their ear, or at least recognize which ear the device is near, also enables certain functionality to be specified or adjusted without requiring the user to perform an additional step, such as to login or hold the device at a specific location to take a picture, etc. In at least some embodiments, the pattern matching can account for at least some effects due to orientation differences or motion blur.

In various embodiments, a device can alter the function of certain elements and/or the location of certain functionality based at least in part upon the ear detected by the device. For example, the device 300 in FIG. 3(a) has a first set of buttons 302 on one edge of the device and a second set of buttons 304 on the opposite edge of the device. When a user holds up a phone to that user's right ear, assuming the side with the camera 306 is facing the user, the user will typically hold that device in the user's right hand and have the user's thumb over the second set of buttons 304. Using similar assumptions, the user's thumb of the left hand will typically be over the first set of buttons 302 if the device is being held up to the user's left ear. Knowing these likelihoods, the device can set the functionality of each set of buttons based upon the detected ear near the device.

Figure 3A:
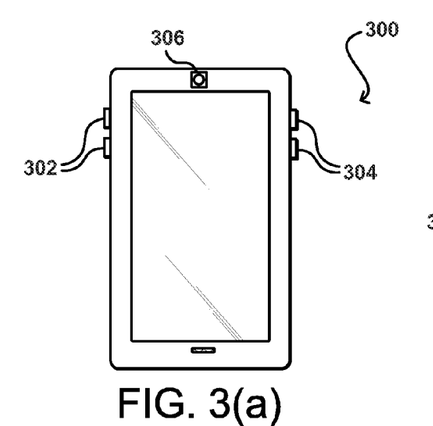
FIGS. 3(a) and 3(b) illustrate different input approaches that can be enabled upon matching ear information in accordance with various embodiments.

For example, a user might want to have quick access to volume controls. If the user's thumb is likely over the second set of buttons 304, the device can set the volume controls to those buttons to make it easier for the user. Similarly, if the user is listening to messages then the device might select certain buttons to enable the user to move forward and backward through the messages based upon which buttons are likely to be easiest for the user to use under the determined conditions.

Figure 3B:
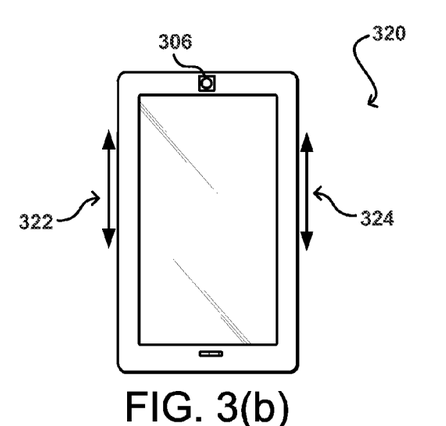

FIG. 3(b) illustrates a device 320 which instead has touch sensitive material on at least the edges of the device. When the camera 306 captures at least one image that can identify information about an ear near the device, the inputs associated to regions on the device can update as well. For example, if the user is holding the device in the user's right hand near the user's right ear, an area 324 of the device near where the user's thumb is likely resting can be assigned to a certain input such as volume adjustment in response to a swipe or other such motion, while the other side 322 can be activated for use near the other ear. An advantage to such an approach is that the device can switch operation to the most convenient operation for the same user when the user switches hands/ears.

It should be understood that users can override such selections and inputs for any of a number of reasons. For example, the user might have a physical limitation or unique way of holding or supporting the device which can lend itself to another input scheme. Further, a user might prefer to have certain types of functionality assigned to specific buttons or inputs.

As discussed, a device can also identify a specific user based at least in part upon the captured ear information. The ability to recognize a specific user enables specific settings or functionality to be set, loaded, adjusted, or otherwise specified for that user. For example, the user might not want volume controls on the physical buttons at all, but might prefer speed dial inputs, menu access, or any of a number of other such inputs. The ability to customize certain inputs is well known in the art and will not be discussed in detail herein. In this situation, however, the device is able to associate those custom or preferred inputs with user ear information, such that when that ear information is detected within a certain distance of the device the preferences for that customer can be loaded or set. For any other user, a default control scheme or right/left ear scheme can be used, except where that user also has a control scheme set with the device, or at least accessible to the device. In some embodiments, a device is able to send information (e.g., contour or point patterns) to a central location that can attempt to identify a user, and in at least some of these embodiments control or other preferences for that user then can be sent to the appropriate device.

In addition to selecting or remapping inputs, any other appropriate customization of the device or interface can be utilized as well upon user identification. For example, default screens, menus, or images can be loaded, certain applications executed, and certain other values specified. Further, custom ring tones or event calendars can be loaded for the identified user. The ability to receive calls can be updated, and where possible calls for that particular user can be routed to and/or received by that device. Any of a number of other such customizations can be used as well within the scope of various embodiments.

In addition to identifying a user, other information can be determined using the captured ear information. For example, a device can determine a relative distance between the user and the device based at least in part upon the relative size of the ear in a captured image. In certain instances, it can be desirable to train the user to hold the device at a certain distance or within a specific range of distances. For example, it can be desirable to hold the device far enough away that the imaging element can capture enough of the ear to perform matching, such as about one inch away. Further, some users may worry about the exposure to radio frequency radiation so it can be desirable to those users to hold the device a minimum distance away in an attempt to reduce exposure to such radiation, whether actually harmful or not.

Figure 4A:
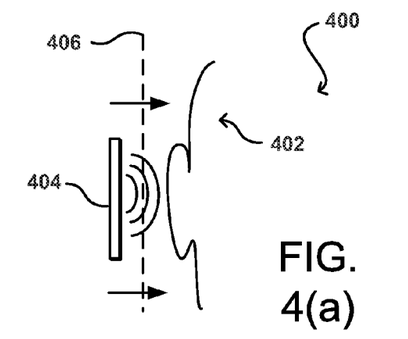
FIGS. 4(a), 4(b), and 4(c) illustrate example situations where an electronic device can adjust functionality in accordance with various embodiments.
Figure 4B:
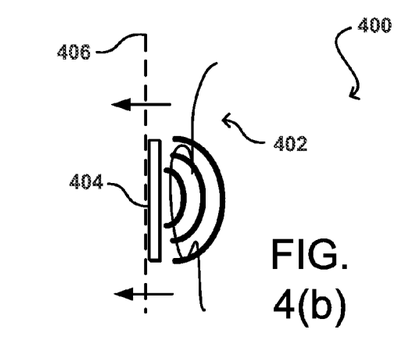

An approach in accordance with one embodiment can adjust the volume of the device in an attempt to control the distance at which the user holds the device. For example, consider the situation 400 of FIG. 4(*a*). In this example, the vertical line 406 represents the target distance for the device 404 relative to the ear of the user 402 during operation. In this example, the device is further away than the target distance 406, so the device can reduce the volume to attempt to have the user bring the device closer. In the example situation 420 of FIG. 4(*b*), the device 404 is closer to the user 402 than the target distance 406, so the device can increase the volume in an attempt to have the user move the device further away. In at least some embodiments, the user has the ability to activate or deactivate this capability and/or set the target distance.

Also, the ability of the device to recognize a user based on ear information enables the device to track use of the device. For example, and if activated, a device can track who used the device and when. For phones, a phone could potentially track information such as who answered a call, placed a call, etc. A log of information could be stored such that the user could see who used the phone, the last time a particular user called a certain number, or other such information.

Also, the ability to recognize a user can enable the user to lockout certain functionality for other users. For example, the user might lockout access to certain data or the ability to place international calls if the person using the device is not determined to be the user. In some cases, a device such as a phone can be locked and might not provide access at all until some sort of authentication is performed indicating that the user is utilizing the device.

As mentioned, in some embodiments a user must go through an initial ear recognition process in order to utilize ear-based authentication. In some embodiments, it might be sufficient for ear information to be captured while a user is logged into, or otherwise authenticated to, the device. In other embodiments, the user must hold the device in a certain orientation until the device is able to obtain sufficient information, such as by emitting an audible notification when an image has been captured and sufficiently analyzed to obtain data necessary for matching. In at least some embodiments, a model of that user's ear can be generated for mapping purposes, which can help with mapping from different angles if the model is three-dimensional. Further, if the user is a growing child the model can update over time as small changes in ear dimension occur, etc.

In some embodiments, a device can make adjustments if an ear is unable to be detected. For example, if based on orientation, operation, and/or hand position the device determines it is likely near a user's ear, but is unable to see the ear, the device can generate a notification or otherwise prompt the user to expose the ear to the device. In other embodiments, the device might activate a speaker mode or adjust some other such functionality. The device can also increase the default volume if the ear might be obstructed by hair or a hat, for example.

Figure 4C:
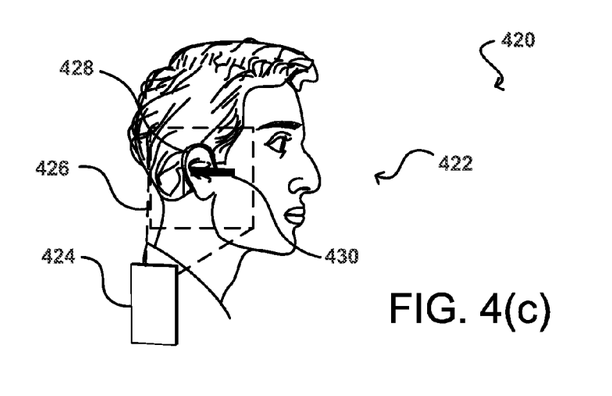

In some instances, an electronic device 424 might detect in the captured image area 426 that the user 422 is wearing an earpiece 430 on the imaged ear 428, as illustrated in the example of FIG. 4(*c*). If the device detects that the user has an earpiece or Bluetooth headset in, for example, the phone can notify the user that the user is wearing the earpiece and should either remove the earpiece or not hold up the phone to the user's ear. In some embodiments where the device recognizes the earpiece, the device can connect to, or pair with, the earpiece and utilize the earpiece if the earpiece is not currently connected (electronically) to the device. If the device is coupled to an earpiece and the user is holding the device up to an ear that does not include an earpiece, the device can automatically disconnect from the earpiece and/or utilize a speaker of the device. Various other modes of operation can be utilized as well within the scope of the various embodiments.

In some instances, an electronic device might capture image information that includes earrings or other objects that obscure at least a portion of the user's ear, or that might otherwise affect the ability to match the ear to existing user image information. A user might change earrings often, which might affect the ability to consistently match the captured image information. In many instances, there will be enough information available to match the image of the ear, as matching algorithms can often successfully identify a user based upon only a portion of an ear. If the user cannot be identified due to a lack of usable information in the image, the user can be asked to remove the obstruction or the device can utilize the right/left ear customization. In some embodiments, a user might only be able to wear a certain earring or type of earring while using ear recognition. Various other options can be utilized as well.

Figure 5:
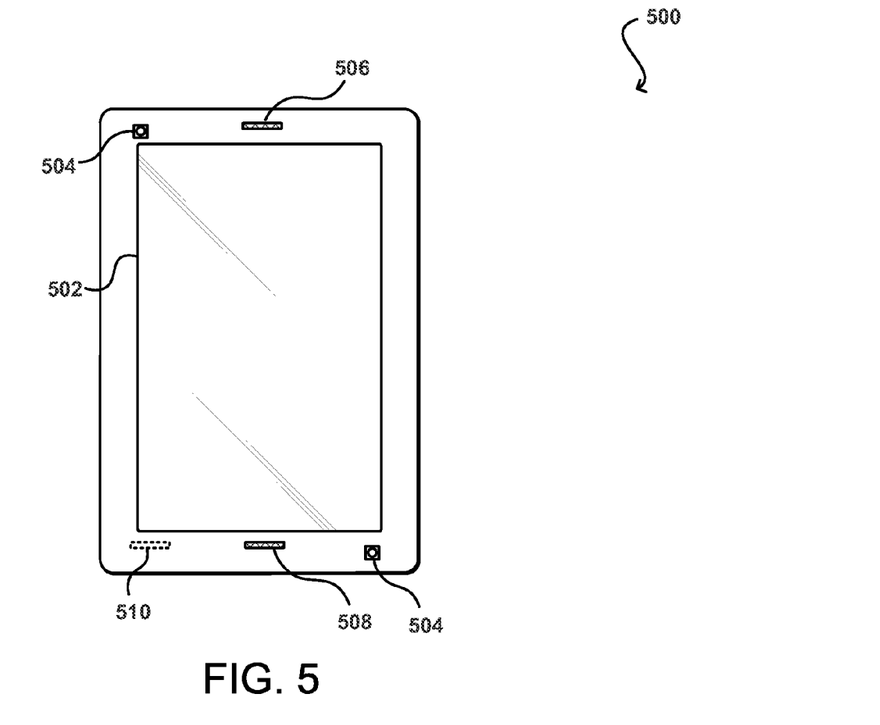
FIG. 5 illustrates an example computing device including elements operable to capture gaze information that can be used in accordance with various embodiments.

FIG. 5 illustrates an example device 500 wherein at least one imaging element 504 of the device is positioned to likely be able to capture information about a user when that user operates the device 500 in a certain mode. Although a portable computing device (e.g., a smart phone, an electronic book reader, or tablet computer) is shown, it should be understood that any device capable of receiving and processing input can be used in accordance with various embodiments discussed herein. The devices can include, for example, desktop computers, notebook computers, electronic book readers, personal data assistants, cellular phones, video gaming consoles or controllers, television set top boxes, and portable media players, among others.

During a phone call, for example, a user will likely hold the device such that the microphone element 508 is near the user's mouth and the speaker element 506 is near the user's ear. Accordingly, at least one imaging element 504 can be positioned with respect to the speaker such that at or around the time in which the user is involved in the call the imaging element 504 is able to capture image information including at least a portion of an ear of the user. In this example, the device includes a pair of imaging elements 504 positioned to attempt to capture ear information from at least two angles in an attempt to determine dimension information in three dimensions, helpful in generating a three-dimensional model of the ear. In some embodiments, an orientation-determining element 510 can be used to assist in determining movement and orientation. For example, an accelerometer or inertial sensor can detect movement of the device, which can activate an image capture mode of the device to attempt to determine ear location, etc. Further, determining that the user's ear is within a certain distance can also be used to deactivate certain functionality, such as to turn off a display element 502 and/or lock out touch input on the display element. In addition to other approaches discussed herein, an element such as a proximity sensor can be used to determine a distance between a user and an electronic device, which can be used to activate or deactivate various functionality, including image capture and analysis.

Figure 6:
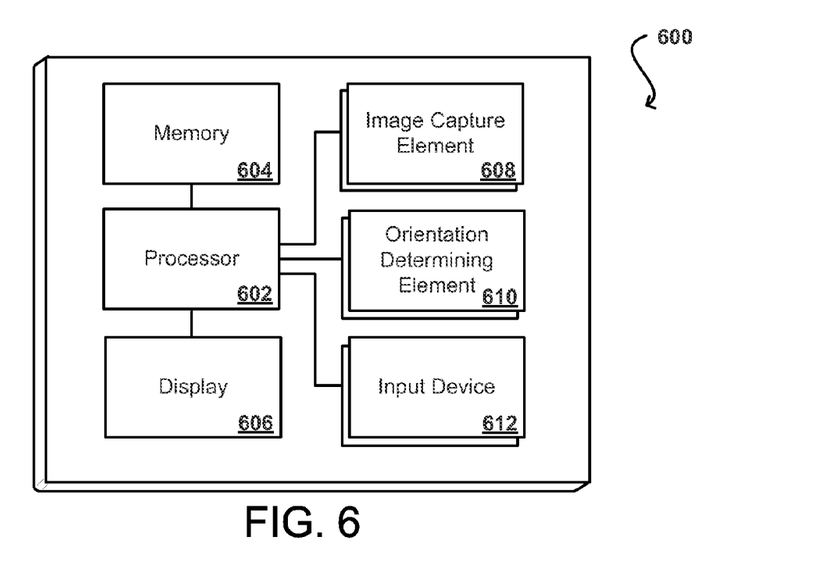
FIG. 6 illustrates example components of a computing device such as that illustrated in FIG. 5.

FIG. 6 illustrates a set of basic components of a computing device 600 such as the device 500 described with respect to FIG. 5. In this example, the device includes at least one processor 602 for executing instructions that can be stored in a memory device or element 604. As would be apparent to one of ordinary skill in the art, the device can include many types of memory, data storage or computer-readable media, such as a first data storage for program instructions for execution by the processor 602, the same or separate storage can be used for images or data, a removable memory can be available for sharing information with other devices, and any number of communication approaches can be available for sharing with other devices. The device typically will include some type of display element 606, such as a touch screen, electronic ink (e-ink), organic light emitting diode (OLED) or liquid crystal display (LCD), although devices such as portable media players might convey information via other means, such as through audio speakers. As discussed, the device in many embodiments will include at least one image capture element 608, such as at least one camera that is able to image a user, people, or objects in the vicinity of the device. An image capture element can include any appropriate technology, such as a CCD or MOS image capture element having a sufficient resolution, focal range and viewable area, to capture an image of the user when the user is operating the device. Methods for capturing images or video using an image capture element with a computing device are well known in the art and will not be discussed herein in detail. It should be understood that image capture can be performed using a single image, multiple images, periodic imaging, continuous image capturing, image streaming, etc.

Further, a device can include the ability to start and/or stop image capture, such as when receiving a command from a user or an application, or detecting specific movement. In some embodiments, a device can include an infrared detector or motion sensor, for example, which can be used to activate an imaging element, image analysis, etc. For example, a device might not capture and analyze image information when there is not a user in the room. If an infrared detector (i.e., a detector with one-pixel resolution that detects changes in state) detects a user entering the room, for example, the device can activate a camera in an attempt to locate the user, perform image analysis, etc.

The device can include at least one additional input device 612 able to receive conventional input from a user. This conventional input can include, for example, a push button, touch pad, touch screen, wheel, joystick, keyboard, mouse, trackball, keypad or any other such device or element whereby a user can input a command to the device. These I/O devices could even be connected by a wireless infrared or Bluetooth or other link as well in some embodiments. In some embodiments, however, such a device might not include any buttons at all and might be controlled only through a combination of visual and audio commands such that a user can control the device without having to be in contact with the device.

Figure 7:
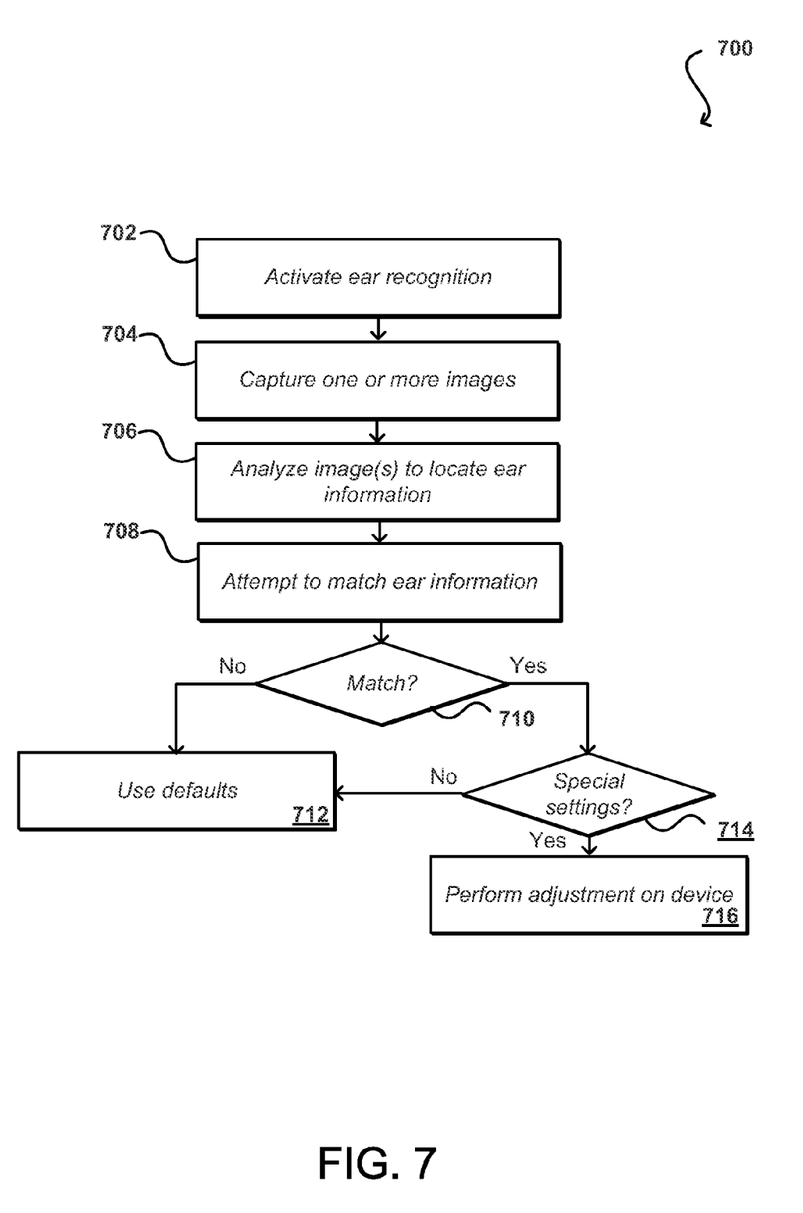
FIG. 7 illustrates an example process for determining device settings using captured ear information that can be used in accordance with various embodiments.

FIG. 7 illustrates an example of a process 700 for utilizing ear recognition that can be utilized in accordance with various embodiments. It should be understood that, for any process discussed herein, there can be additional, fewer, or alternative steps performed in similar or alternative orders, or in parallel, within the scope of the various embodiments unless otherwise stated. Further, it should be understood that other user features can be utilized as well in accordance with various embodiments. In this example, an ear recognition mode is activated for an electronic device 702. In some embodiments the user must activate this mode manually, while in other embodiments the device activates this mode automatically upon satisfaction of at least one criterion. For example, upon detection of the device being picked up, the user placing his or her hand on the device, a call being placed/received, or a specific application being launched, the ear recognition mode can be activated. As discussed, one or more images will be captured while the mode is activated 704. In certain embodiments, images or video will be captured until a portion of at least one image is determined to match ear information to at least a minimum degree of certainty or other such threshold. In other embodiments, images will continue to be captured periodically based on movement or a number of other factors as discussed elsewhere herein. At least one image is analyzed using at least one algorithm discussed above to attempt to locate ear information 706. In at least one embodiment, this can include analyzing images until at least one shape or set of points is located that matches parameters for a human ear. When at least one such image is located, the device can attempt to match at least a portion of the image with ear information 708, such as by performing pattern or feature matching. As discussed, this can involve determining whether the ear is a right or left ear, and/or can involve attempting to determine an identity of the user based on ear information (e.g., a 3D model) stored for that user.

If no match is found, such as where there is no matching user information or no determination as to which ear is nearest can be made with an acceptable level of accuracy 710, default settings can be utilized for the device 712. In at least some embodiments, this can involve leaving the current settings or loading a set of default values or inputs. If there is a match, a determination is made as to whether there are any adjustments or special settings that should be made based upon the match 714. If the ear is determined to be a right ear, for example, inputs can be set to favor a user holding the device with a right hand, for example. If the match is for a specific user, any special adjustment can be made based on the recognition 716. As discussed, a user can have the option of activating or deactivating such functionality, and/or adjusting the settings for any determined match.

Figure 8:
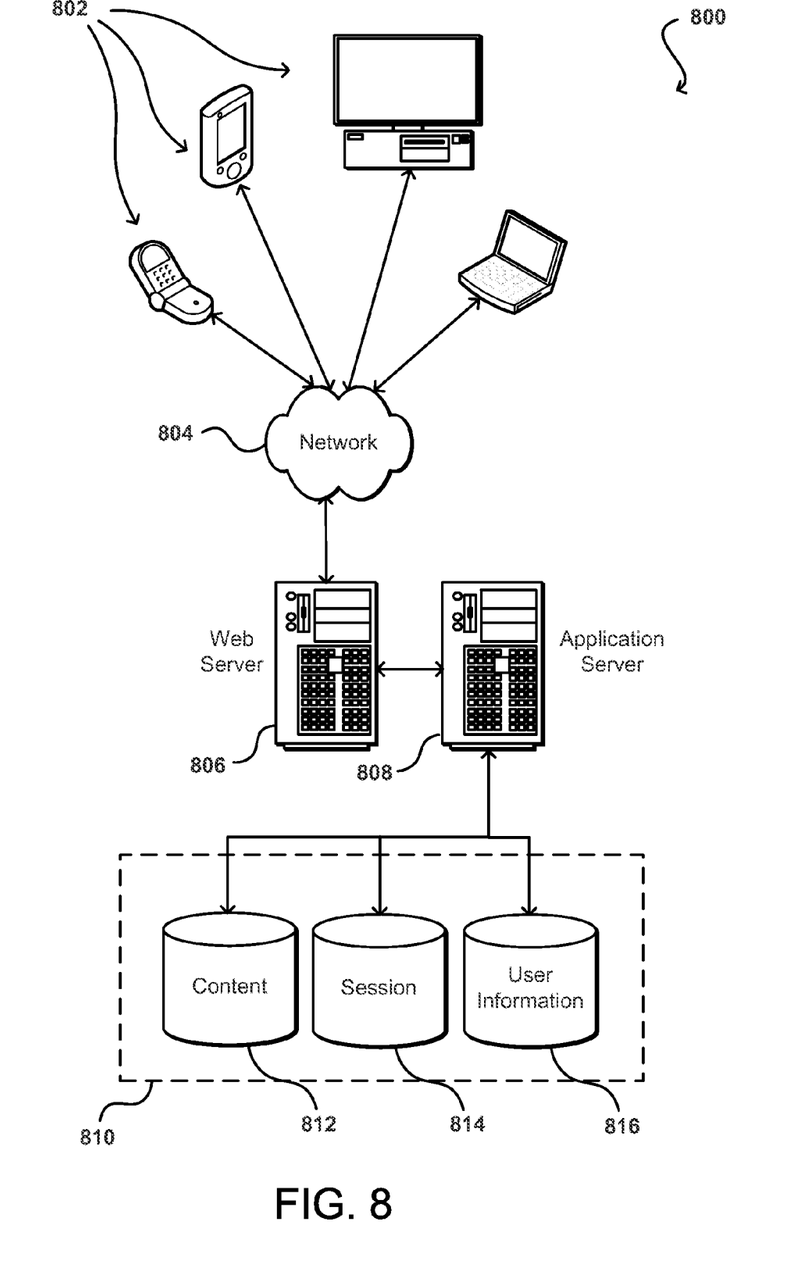
FIG. 8 illustrates an environment in which various embodiments can be implemented.

As discussed, different approaches can be implemented in various environments in accordance with the described embodiments. For example, FIG. 8 illustrates an example of an environment 800 for implementing aspects in accordance with various embodiments. As will be appreciated, although a Web-based environment is used for purposes of explanation, different environments may be used, as appropriate, to implement various embodiments. The system includes an electronic client device 802, which can include any appropriate device operable to send and receive requests, messages or information over an appropriate network 804 and convey information back to a user of the device. Examples of such client devices include personal computers, cell phones, handheld messaging devices, laptop computers, set-top boxes, personal data assistants, electronic book readers and the like. The network can include any appropriate network, including an intranet, the Internet, a cellular network, a local area network or any other such network or combination thereof. Components used for such a system can depend at least in part upon the type of network and/or environment selected. Protocols and components for communicating via such a network are well known and will not be discussed herein in detail. Communication over the network can be enabled via wired or wireless connections and combinations thereof. In this example, the network includes the Internet, as the environment includes a Web server 806 for receiving requests and serving content in response thereto, although for other networks, an alternative device serving a similar purpose could be used, as would be apparent to one of ordinary skill in the art.

The illustrative environment includes at least one application server 808 and a data store 810. It should be understood that there can be several application servers, layers or other elements, processes or components, which may be chained or otherwise configured, which can interact to perform tasks such as obtaining data from an appropriate data store. As used herein, the term "data store" refers to any device or combination of devices capable of storing, accessing and retrieving data, which may include any combination and number of data servers, databases, data storage devices and data storage media, in any standard, distributed or clustered environment. The application server 808 can include any appropriate hardware and software for integrating with the data store 810 as needed to execute aspects of one or more applications for the client device and handling a majority of the data access and business logic for an application. The application server provides access control services in cooperation with the data store and is able to generate content such as text, graphics, audio and/or video to be transferred to the user, which may be served to the user by the Web server 806 in the form of HTML, XML or another appropriate structured language in this example. The handling of all requests and responses, as well as the delivery of content between the client device 802 and the application server 808, can be handled by the Web server 806. It should be understood that the Web and application servers are not required and are merely example components, as structured code discussed herein can be executed on any appropriate device or host machine as discussed elsewhere herein.

The data store 810 can include several separate data tables, databases or other data storage mechanisms and media for storing data relating to a particular aspect. For example, the data store illustrated includes mechanisms for storing content (e.g., production data) 812 and user information 816, which can be used to serve content for the production side. The data store is also shown to include a mechanism for storing log or session data 814. It should be understood that there can be many other aspects that may need to be stored in the data store, such as page image information and access rights information, which can be stored in any of the above listed mechanisms as appropriate or in additional mechanisms in the data store 810. The data store 810 is operable, through logic associated therewith, to receive instructions from the application server 808 and obtain, update or otherwise process data in response thereto. In one example, a user might submit a search request for a certain type of item. In this case, the data store might access the user information to verify the identity of the user and can access the catalog detail information to obtain information about items of that type. The information can then be returned to the user, such as in a results listing on a Web page that the user is able to view via a browser on the user device 802. Information for a particular item of interest can be viewed in a dedicated page or window of the browser.

Each server typically will include an operating system that provides executable program instructions for the general administration and operation of that server and typically will include computer-readable medium storing instructions that, when executed by a processor of the server, allow the server to perform its intended functions. Suitable implementations for the operating system and general functionality of the servers are known or commercially available and are readily implemented by persons having ordinary skill in the art, particularly in light of the disclosure herein.

The environment in one embodiment is a distributed computing environment utilizing several computer systems and components that are interconnected via communication links, using one or more computer networks or direct connections. However, it will be appreciated by those of ordinary skill in the art that such a system could operate equally well in a system having fewer or a greater number of components than are illustrated in FIG. 8. Thus, the depiction of the system 800 in FIG. 8 should be taken as being illustrative in nature and not limiting to the scope of the disclosure.

The various embodiments can be further implemented in a wide variety of operating environments, which in some cases can include one or more user computers or computing devices which can be used to operate any of a number of applications. User or client devices can include any of a number of general purpose personal computers, such as desktop or laptop computers running a standard operating system, as well as cellular, wireless and handheld devices running mobile software and capable of supporting a number of networking and messaging protocols. Such a system can also include a number of workstations running any of a variety of commercially-available operating systems and other known applications for purposes such as development and database management. These devices can also include other electronic devices, such as dummy terminals, thin-clients, gaming systems and other devices capable of communicating via a network.

Most embodiments utilize at least one network that would be familiar to those skilled in the art for supporting communications using any of a variety of commercially-available protocols, such as TCP/IP, OSI, FTP, UPnP, NFS, CIFS and AppleTalk. The network can be, for example, a local area network, a wide-area network, a virtual private network, the Internet, an intranet, an extranet, a public switched telephone network, an infrared network, a wireless network and any combination thereof.

In embodiments utilizing a Web server, the Web server can run any of a variety of server or mid-tier applications, including HTTP servers, FTP servers, CGI servers, data servers, Java servers and business application servers. The server(s) may also be capable of executing programs or scripts in response requests from user devices, such as by executing one or more Web applications that may be implemented as one or more scripts or programs written in any programming language, such as Java®, C, C# or C++ or any scripting language, such as Perl, Python or TCL, as well as combinations thereof. The server(s) may also include database servers, including without limitation those commercially available from Oracle®, Microsoft®, Sybase® and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of embodiments, the information may reside in a storage-area network (SAN) familiar to those skilled in the art. Similarly, any necessary files for performing the functions attributed to the computers, servers or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch-sensitive display element or keypad) and at least one output device (e.g., a display device, printer or speaker). Such a system may also include one or more storage devices, such as disk drives, optical storage devices and solid-state storage devices such as random access memory (RAM) or read-only memory (ROM), as well as removable media devices, memory cards, flash cards, etc.

Such devices can also include a computer-readable storage media reader, a communications device (e.g., a modem, a network card (wireless or wired), an infrared communication device) and working memory as described above. The computer-readable storage media reader can be connected with, or configured to receive, a computer-readable storage medium representing remote, local, fixed and/or removable storage devices as well as storage media for temporarily and/or more permanently containing, storing, transmitting and retrieving computer-readable information. The system and various devices also typically will include a number of software applications, modules, services or other elements located within at least one working memory device, including an operating system and application programs such as a client application or Web browser. It should be appreciated that alternate embodiments may have numerous variations from that described above. For example, customized hardware might also be used and/or particular elements might be implemented in hardware, software (including portable software, such as applets) or both. Further, connection to other computing devices such as network input/output devices may be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules or other data, including RAM, ROM, EEPROM, flash memory or other memory technology, CD-ROM, digital versatile disk (DVD) or other optical storage, magnetic cassettes, magnetic tape, magnetic disk storage or other magnetic storage devices or any other medium which can be used to store the desired information and which can be accessed by a system device. Based on the disclosure and teachings provided herein, a person of ordinary skill in the art will appreciate other ways and/or methods to implement the various embodiments.

The specification and drawings are, accordingly, to be regarded in an illustrative rather than a restrictive sense. It will, however, be evident that various modifications and changes may be made thereunto without departing from the broader spirit and scope of the invention as set forth in the claims.

What is claimed is:

1. A method of adjusting functionality of an electronic device, comprising:
    detecting a type of movement and orientation of the electronic device, the type of movement being associated with a change in user position relative to the electronic device;
    based at least in part on the type of movement, determining that a distance between a user and the electronic device is less than a certain distance;
    activating image capture of the electronic device;
    capturing image information of at least a portion of an ear of the user;
    analyzing, using a processor of the electronic device, the image information to determine at least one portion of the captured image information including a view of at least a portion of an ear of the user, wherein the image information includes a first image that includes a first view of the ear captured at a first angle, and wherein the image information includes a second image that includes a second view of the ear captured at a second angle;
    generate biometric information representative of the portion of the ear based at least in part on the first image and the second image;
    comparing the biometric information to ear shape information stored for at least one user to attempt to determine an identity of the user;
    determining personalized functionality of the electronic device based at least in part on the identity of the user and the one of the type of movement and the orientation of the electronic device; and
    adjusting at least one aspect of the electronic device in accordance with the personalized functionality and the distance between the user and the electronic device.

2. The method of claim 1, wherein comparing data in the at least one portion to ear shape information stored for at least one user includes extracting feature information from the at least one portion and matching the feature information against the ear shape information.

3. The method of claim 1, wherein determining the identity of the user includes at least one of performing pattern matching or feature matching, or utilizing at least one user model to attempt to match information in the captured image information to information for the ear of the user.

4. The method of claim 1, further comprising:
    automatically activating the capturing of image information upon determining that a user is moving the electronic device or moving relative to the electronic device.

5. The method of claim 4, wherein the determining that the user is moving the electronic device is determined using at least one of an accelerometer, an electronic gyroscope, a proximity sensor, or an inertial sensor.

6. The method of claim 1, wherein adjusting at least one aspect of the electronic device includes adjusting a position of at least one input of the electronic device.

7. The method of claim 1, wherein adjusting at least one aspect of the electronic device includes adjusting a functionality of at least one input of the electronic device.

8. The method of claim 7, wherein the at least one input includes at least one of a volume control, a call control, a device control, and a navigational control.

9. The method of claim 1, wherein adjusting at least one aspect of the electronic device includes loading customized interface settings for the identified user.

10. The method of claim 1, further comprising:
in response to being unable to determine the identity of the user, adjusting at least one aspect of the electronic device,
wherein an unidentified user is unable to access certain functionality of the electronic device.

11. The method of claim 1, further comprising:
capturing at least one image of at least one ear of the user; and
generating a two- or three-dimensional model of at least the portion of the ear useful in matching ear information.

12. The method of claim 1, wherein the movement corresponds to movement of the device to an ear of the user of the electronic device, and wherein the movement is determined using at least one of an orientation or position-determining element of the electronic device.

13. A computer-implemented method of adjusting functionality of an electronic device, comprising:
under control of one or more computer systems configured with executable instructions,
detecting a type of movement and orientation of the electronic device, the type of movement being associated with a change in user position relative to the electronic device;
based at least in part on the type of movement, determining that a distance between a user and the electronic device is less than a certain distance;
activating image capture of the electronic device;
capturing image information of at least a portion of an ear of the user using at least one image capture element, wherein the image information includes a first image that includes a first view of the ear captured at a first angle, and wherein the image information includes a second image that includes a second view of the ear captured at a second angle;
generating biometric information representative of the portion of the ear based at least in part on the first image and the second image;
determining whether the biometric information represents a right ear or a left ear;
determining a first functionality of the electronic device based at least in part on the type of movement, the orientation of the electronic device, and the biometric information representing the right ear;
determining a second functionality of the electronic device based at least in part on the type of movement, the orientation of the electronic device, and the biometric information representing the left ear; and
automatically adjusting at least one aspect of the electronic device in accordance with one of the first functionality or the second functionality and the distance between the user and the electronic device.

14. The computer-implemented method of claim 13, wherein adjusting at least one aspect of the electronic device includes adjusting a position of at least one input of the electronic device.

15. The computer-implemented method of claim 13, wherein adjusting at least one aspect of the electronic device includes adjusting a functionality of at least one input of the electronic device.

16. The computer-implemented method of claim 15, wherein the at least one input includes at least one of a volume control, a call control, and a navigational control.

17. A computing device, comprising:
a processor;
at least one image capture element; and
a memory device including instructions operable to be executed by the processor to perform a set of actions, enabling the computing device to:
detect a type of movement and orientation of the computing device, the type of movement being associated with a change in user position relative to the computing device;
based at least in part on the type of movement, determining that a distance between a user and the computing device is less than a certain distance;
activate image capture of the computing device;
capture image information of at least a portion of an ear of the user using at least one image capture element, wherein the image information includes a first image that includes a first view of the ear captured at a first angle, and wherein the image information includes a second image that includes a second view of the ear captured at a second angle;
generate biometric information representative of the portion of the ear based at least in part on the first image and the second image;
determine personalized functionality of the computing device based at least in part on the biometric information and the type of movement and the orientation of the computing device; and
adjust at least one aspect of the computing device in accordance with the personalized functionality and the distance between the user and the computing device.

18. The computing device of claim 17, wherein the at least one aspect of the at least the portion of the ear includes at least one of an identity of the user having that ear, whether the ear is a right ear or a left ear, and a distance to the ear from the computing device.

19. The computing device of claim 17, wherein the at least one image capture element includes at least one of a digital still camera or digital video camera.

20. The computing device of claim 19, wherein adjusting at least one aspect of the computing device includes at least one of adjusting a position of at least one input of the computing device or adjusting a functionality of at least one input of the computing device.

21. A non-transitory computer-readable storage medium storing processor-executable instructions for adjusting an electronic device, comprising:
program code for detecting a type of movement and orientation of the electronic device, the type of movement being associated with a change in user position relative to the electronic device;
program code for, based at least in part on the type of movement, determining that a distance between a user and the electronic device is less than a certain distance;
program code for activating image capture of the electronic device;
program code for capturing image information of at least a portion of an ear of the user using at least one image capture element;

program code for analyzing, using a processor of the electronic device, the captured image information to determine at least one portion of the captured image information including a view of at least a portion of an ear of the user, wherein the image information includes a first image that includes a first view of the ear captured at a first angle, and wherein the image information includes a second image that includes a second view of the ear captured at a second angle;

program code for generating biometric information representative of the portion of the ear based at least in part on the first image and the second image;

program code for determining personalized functionality of the electronic device based at least in part on the biometric information and the type of movement and the orientation of the electronic device; and program code for adjusting at least one aspect of the electronic device in accordance with the personalized functionality and the distance between the user and the electronic device.

22. The non-transitory computer-readable storage medium of claim 21, wherein the at least one aspect of the at least the portion of the ear includes at least one of an identity of the user having that ear, whether the ear is a right ear or a left ear, and a distance to the ear from the electronic device.

23. The non-transitory computer-readable storage medium of claim 21, wherein adjusting at least one aspect of the electronic device includes at least one of adjusting a position of at least one input of the electronic device or adjusting a functionality of at least one input of the electronic device.

24. The non-transitory computer-readable storage medium of claim 21, further comprising:

program code for capturing at least one image of at least one ear of the user, and program code for generating a two- or three-dimensional model of the at least one ear useful in matching ear information.

* * * * *